United States Patent
Zheng

(10) Patent No.: US 8,470,554 B2
(45) Date of Patent: Jun. 25, 2013

(54) PROKARYOTIC EXPRESSION OF SOLUBLE, ACTIVE DKK

(75) Inventor: Jie Zheng, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 112 days.

(21) Appl. No.: 13/133,474

(22) PCT Filed: Dec. 18, 2009

(86) PCT No.: PCT/US2009/069628
§ 371 (c)(1),
(2), (4) Date: Jun. 8, 2011

(87) PCT Pub. No.: WO2010/075194
PCT Pub. Date: Jul. 1, 2010

(65) Prior Publication Data
US 2011/0244518 A1     Oct. 6, 2011

Related U.S. Application Data

(60) Provisional application No. 61/139,711, filed on Dec. 22, 2008.

(51) Int. Cl.
| | |
|---|---|
| *C12P 21/06* | (2006.01) |
| *C12N 15/00* | (2006.01) |
| *C12N 1/20* | (2006.01) |
| *C07H 21/02* | (2006.01) |
| *C07K 14/00* | (2006.01) |

(52) U.S. Cl.
USPC .................. 435/69.1; 435/320.1; 435/252.3; 536/23.1; 530/350

(58) Field of Classification Search
USPC .... 435/69.1, 320.1, 252.3; 536/23.1; 530/350
See application file for complete search history.

(56) References Cited

PUBLICATIONS

Chen et al. Jun. 3, 2008; Structural insight into the mechanisms of Wnt signaling antagonist by Dkk. J. Biol. Chem 283(34): 23364-23370.*
Wong et al. 2000; Structural basis of the recognition of the Dishevelled DEP domain in the Wnt signaling pathway. Nature Structural Biology. 7(12): 1178-1184.*
Novagen S-Tag System 1993; at wolfson.huji.ac.il/expression/local/STag_system.pdf.*
Brott, B. K. and Sokol, S. Y. "Regulation of Wnt/LRP Signaling by Distinct Domains of Dickkopf Proteins" Molecular and Cellular Biology 2002 22(17):6100-6110.
Gregory et al. "The Wnt Signaling Inhibitor Dickkopf-1 Is Required for Reentry into the Cell Cycle of Human Adult Stem Cells from Bone Marrow" The Journal of Biological Chemistry 2003 278(30):28067-28078.
Krupnik et al. "Functional and Structural Diversity of the Human Dickkopf Gene Family" Gene 1999 238:301-313.
Li et al. "Second Cysteine-rich Domain of Dickkopf-2 Activates Canonical Wnt Signaling Pathway via LRP-6 Independently of Dishevelled" The Journal of Biological Chemistry 2002 277(8):5977-5981.
Mao, B. and Niehrs, C. "Kremen2 Modulates Dickkopf2 Activity during Wnt/LRP6 Signaling" Gene 2003 302:179-183.
Mao et al. "LDL-receptor-related Protein 6 Is a Receptor for Dickkopf Proteins" Nature 2001 411:321-325.
Semënov et al. "Head Inducer Dickkopf-1 Is a Ligand for Wnt Coreceptor LRP6" Current Biology 2001 11:951-961.

* cited by examiner

*Primary Examiner* — Karen Cocharne Carlson
(74) *Attorney, Agent, or Firm* — Licata & Tyrrell P.C.

(57) ABSTRACT

Dickkopf (Dkk) proteins inhibit the canonical Wnt signaling pathway. Each of the members of the Dkk family has been previously cloned and expressed as a soluble protein in eukaryotic cells, while expression in bacterial cells has resulted in the formation of insoluble inclusion bodies that require further processing. The present invention provides compositions and methods for producing soluble, active dkk protein in prokaryotic host cells, by expressing the dkk protein as a fusion protein with a solubilization molecule, thereby providing an inexpensive and convenient source of pure active Dkk.

24 Claims, 2 Drawing Sheets

PROKARYOTIC EXPRESSION OF SOLUBLE, ACTIVE DKK

INTRODUCTION

This application is a U.S. National Stage Application of PCT/US2009/068628 filed Dec. 18, 2009 and claims the benefit of priority of U.S. Provisional Application No. 61/139,711, filed Dec. 22, 2008, the contents of each of which are incorporated herein by reference in their entirety.

This research underlying this invention was supported in part with funds from National Institutes of Health grant no. GM081492. The United States Government has certain rights in this invention.

BACKGROUND OF THE INVENTION

Wnt signaling involves multiple pathways and mediates embryonic induction, generation of cell polarity, specification of cell fate (Cadigan & Nusse (1997) *Genes Dev.* 11(24): 3286-305; Peifer & Polakis (2000) *Science* 287(5458):1606-9), as well as being closely linked to tumorigenesis (Peifer & Polakis (2000) supra). Wnt signaling is also regulated by several types of endogenous antagonists (Kawano & Kypta (2003) *J. Cell Sci.* 116 (Pt 13):2627-34), where Dickkopf (Dkk) is probably the most notable Wnt antagonist inhibiting the canonical Wnt signaling pathway. The initiation of canonical Wnt/β-catenin signaling pathway requires the binding of secreted Wnt proteins to receptor Frizzled (Fz) proteins (Bhanot, et al. (1996) *Nature* 382(6588):225-30) and coreceptor LDL receptor-related protein 5 or 6 (LRP5/6) (Mao, et al. (2001) *Mol. Cell.* 7(4):801-9; Mao, et al. (2001) *Nature* 411(6835):321-5; Pinson, et al. (2000) *Nature* 407(6803):535-8; Tamai, et al. (2000) *Nature* 407(6803):530-5). To block the canonical Wnt signaling pathway, Dkk binds to LRP5/6 and another single transmembrane receptor Kremen simultaneously (Semënov, et al. (2001) *Curr. Biol.* 11(12):951-61; Mao & Niehrs (2003) *Gene* 302(1-2):179-83; Mao, et al. (2001) supra). The ternary DKK-Kremen-LRP5/6 complex not only prevents Wnt from interacting with LRP5/6, but also promotes the rapid internalization and removal of LRP5/6 from plasma membrane, further inhibiting the canonical Wnt signaling (Mao & Niehrs (2003) supra).

Four members of the Dkk family have been identified in mammals (Krupnik, et al. (1999) *Gene* 238(2):301-13). Dkk1, the most extensively studied member, was originally cloned as a molecule that is able to induce secondary axes with a complete head when its mRNA is injected into *Xenopus* embryos together with a dominant-negative mutant of the BMP-2/4 receptor (Glinka, et al. (1998) *Nature* 391(6665):357-62). The characteristic developmental function of Dkk1 is its head-inducing activity in vertebrate embryos (Glinka, et al. (1998) supra), a process that has been postulated to involve inhibition of Wnt signaling (Glinka, et al. (1997) *Nature* 389(6650):517-9).

Members of the Dkk family are composed of two characteristic cysteine-rich domains (CRDs) separated by a variable-length spacer region, each domain containing 10 conserved cysteines (Krupnik, et al. (1999) supra). Both domains remain well conserved among all four members; in particular, Dkk1 and Dkk2 share 50% identity in their N-terminal cysteine-rich region amino acid sequences and 70% identity in their C-terminal regions. Among the four Dkk members, Dkk1 and Dkk4 appear indistinguishable in terms of Wnt antagonist activity, whereas Dkk3 does not appear to modulate Wnt signaling (Krupnik, et al. (1999) *Gene*). However, Dkk2 is more complicated, since it functions as a Wnt activator or a Wnt inhibitor in a cell-context dependent way. On the other hand, previous studies have demonstrated that the C-terminal cysteine-rich domains of Dkk1 and Dkk2 behave similarly to one another in Wnt signaling: in isolation they are both necessary and sufficient for physically associating with LRP5/6 and inhibiting canonical Wnt signaling (Brott & Sokol (2002) *Mol. Cell. Biol.* 22(17):6100-10; Li, et al. (2002) *J. Biol. Chem.* 277(8):5977-81). By contrast, the N-terminal cysteine-rich domain of Dkk1/2 appears to play a regulatory role in these interactions, and likely responsible for the different activities of the intact Dkk1 and Dkk2 proteins (Brott & Sokol (2002) supra).

Despite the important roles of Dkk in regulating Wnt signaling, the particular molecular mechanism that results from Dkk interaction with LRP5/6 is not completely understood. Much of the information on the functions of the various Dkk genes has been derived from studies with cloned versions of Dkk, including the entire Dkk gene as well as portions that comprise only a single CRD domain of Dkk. Thus, the properties of the CRDs have been investigated by isolation of the individual domains and testing their effects upon wnt activity (Li, et al. (2002) supra) as well as more elaborate experiments where fusion proteins were created with the N-terminal CRD of Dkk1 fused to the carboxy-terminal CRD of Dkk2 and vice versa (Brott & Sokol (2002) supra).

In most cases, expression of the Dkk proteins has been limited to eukaryotic expression vectors, while in the case of Dkk1, prokaryotic vectors have also been used (Gregory, et al. (2003) *J. Biol. Chem.* 278:28067-28078; U.S. Patent Application 20080038775). In general, expression of eukaryotic genes in eukaryotic host cells insures the likelihood of the correct folding as well as allowing postsynthetic modifications such as glycosylation or protease cleavages. On the other hand, yields of target proteins are limited, since a large number of different proteins are expressed in the eukaryotic host cells and there are expenses associated with media and growth. In contrast, media for prokaryotic expression is very inexpensive and high yields of proteins can be achieved. The limiting factor in prokaryotic systems is that folding of proteins can be problematic both immediately after synthesis of the proteins as well as in steps that may be carried out at a later stage. The latter effect is due to the expression of the proteins commonly being found in the form of what are called "inclusion bodies", insoluble masses of proteins that require essentially denaturing conditions to render them into soluble functional form.

Thus, although the ultimate yield of functional proteins may be high in prokaryotic systems, the specific activity may be much lower since a large number of inactive forms may be present as well. In some cases, the presence of the inactive forms is irrelevant since they may simply act as passive carriers, but other studies, such as crystallographic studies or binding experiments, depend upon the availability of purified highly active forms. Further problems are also specifically seen with the prokaryotically-derived Dkk proteins. For instance, yields of Dkk1 have been reported as being relatively low, with more than 60% of the product containing intermolecular cross-links between two different Dkk molecules (Gregory, et al. (2003) supra), thereby limiting proper intramolecular disulfide bond formation and altering the ultimate configuration of the Dkk protein. Treatment of inclusion bodies with either Guanidine Chloride or Urea (two standard solubilization methods for inclusion bodies) has been suggested; however, the resulting preparations were devoid of activity in both co-immuno-precipitation assays and TCF reporter assays (see U.S. Patent Application 20080038775). As such, there is a need in the art for an inexpensive source of Dkk, which is both soluble and active, for use in screening assays and in the analysis of Dkk and its domains.

SUMMARY OF THE INVENTION

The present invention features a method for producing soluble, active Dickkopf (Dkk) protein, or a fragment thereof. The method involves the steps of
   a) growing a culture of prokaryotic host cells that express all or a portion of a dkk protein encoded by an expression construct;
   b) isolating said prokaryotic host cells;
   c) lysing said prokaryotic host cells;
   d) isolating the soluble portion of said prokaryotic host cell lysate; and
   e) purifying said dkk protein from said soluble portion thereby producing soluble, active Dickkopf (Dkk) protein, or a fragment thereof.

In some embodiments, the step of growing the prokaryotic host cells includes adding IPTG to the culture of cells. In other embodiments, all or a portion of the dkk protein is expressed as part of a fusion protein. In particular embodiments, the fusion protein includes a protein purification tag or solubilization molecule, or a combination thereof, and may further include one or more cleavage sequences. In specific embodiments, the portion of the dkk protein contains only one cysteine-rich domain, wherein said cysteine-rich domain is the carboxy-terminal cysteine-rich domain. In some embodiments, the expression construct is derived from a prokaryotic expression vector and includes such vectors as pET32a. In particular embodiments, the dkk protein is selected from the group of dkk-1, dkk-2, dkk-3 and dkk-4. In specific embodiments, the dkk protein is dkk-2. Prokaryotic host cells of particular use in accordance with the instant method include those having a mutation in the TrxB gene, the gor gene or both said TrxB gene and said gor gene, with some embodiments further embracing a prokaryotic host cell with a mutation in the lacY1 gene. In further embodiments of this method, isolation step (d) is carried out by centrifugation, and purification step (e) includes the use of a metal chelate column and/or an HPLC step.

The present invention also embraces expression constructs and prokaryotic host cells for expressing all or a portion of dkk proteins such as dkk-2. In some embodiments, the dkk-2 protein is part of a fusion protein, which contains sequences such a protein purification tag or a solubilization molecule, or a combination thereof. In other embodiments, the dkk-2 protein is soluble when expressed in a prokaryotic host cell. In particular embodiments, the portion of said dkk protein includes only one cysteine-rich domain of the dkk protein, wherein said cysteine-rich domain is the C-terminal cysteine-rich domain of the dkk protein. In further embodiments, the prokaryotic host cell has a mutation in the TrxB gene, the gor gene or both said TrxB gene and said gor gene.

BRIEF DESCRIPTION OF THE DRAWINGS

Figure depicts the purification profile of DKK2C by HPLC.

DETAILED DESCRIPTION OF THE INVENTION

Figure 1A:
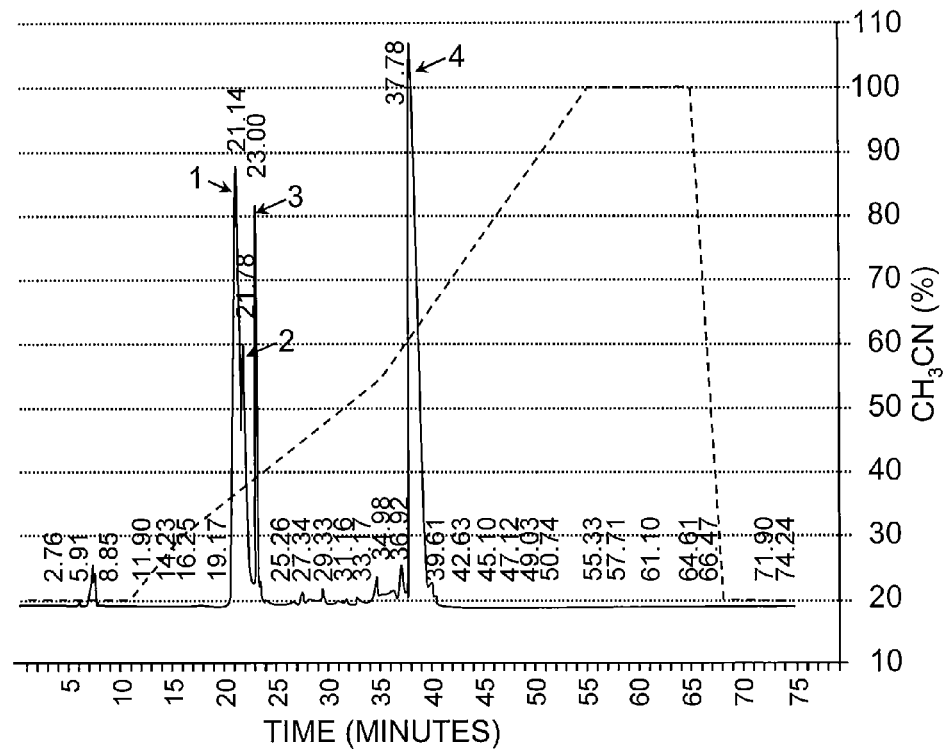
FIG. 1A shows the acetonitrile gradient (dashed line) (flow rate, 2 ml/minute) and HPLC traces (solid line) of proteins after thrombin cleavage of Trx-Dkk2C fusion proteins.

The present invention embraces compositions and methods for expressing and isolating soluble forms of active Dkk from prokaryotic cells. Previous to the present invention, all four members of the Dkk family (Dkk1, Dkk2, Dkk3 and Dkk4) had been expressed as clones in eukaryotic systems, but only Dkk1 has been expressed in bacterial systems and only in the form of insoluble inclusion bodies, which had to be resolubilized to recover active protein. The potential synthesis of Dkk proteins in bacterial systems with the correct structure is complicated by the presence of numerous cysteines in the amino acid sequences; for example each of the two CRD's of Dkk contains 10 cysteines which may be involved in the formation of five separate disulfide bridges. As discussed herein, conventional approaches to express Dkk proteins in prokaryotic cells, such as *E. coli*, has yielded substantially inactive material, likely due to improper refolding of the recombinant protein in these cells. This may be a reflection of the original state of the proteins prior to forming inclusion bodies or may be a consequences of the methodologies used to resolubilize proteins form inclusion bodies. Moreover, it has been noted that dkk proteins can undergo post-translational processing including glycosylation (Fedi, et al. (1999) *J. Biol. Chem.* 274:19465-19472; Krupnik, et al. (1999) supra; U.S. Patent Application 20080038775) and protease cleavage (Krupnik, et al. (1999) supra), events that would only ensue in eukaryotic host cells. In this respect, it has been suggested that a lack of this glycosylation or even an altered glycosylation pattern derived from insect host cells results in significantly less dkk activity compared to the glycosylated version of Dkk1 (U.S. Patent Application 20080038775).

It has now been found that with appropriate expression constructs and host cells, Dkk sequences can be expressed as soluble proteins in prokaryotic host cells and despite the absence of eukaryotic post-translational processing, the resultant proteins maintain high activity. Accordingly, the present invention embraces, expression constructs and prokaryotic host cells, and methods for using the same to produce soluble, active dkk protein, or a fragment thereof.

As is known in the art, Dickkopf (Dkk) is a negative regulator of Wnt signaling (Glinka, et al. (1998) supra; Niehrs (1999) *Trends Genet.* 15(8):314-9). The Dkk protein is secreted and rich in cysteines. Dkk does not bind to Wnt but interacts with the Wnt co-receptor LRP (Mao, et al. (2001) supra; Bafico, et al. (2001) *Nat. Cell Biol.* 3(7):683-6; Semënov, et al. (2001) supra; Nusse (2001) *Nature* 411(6835):255-6). It also binds to a receptor called Kremen, resulting in down-regulation of LRP from the cells surface (Mao, et al. (2002) *Nature* 417(6889):664-7). There are four Dkk members in the human genome. The amino acid sequences of these human proteins are known under GENBANK Accession Nos. NP_036374 (Dkk-1), NP_055236 (Dkk-2), NP_001018067 (Dkk-3) and NP_055235 (Dkk-4). Similarly, Dkk proteins are found in mouse (GENBANK Accession Nos. NP_034181, NP_064661, NP_056629 and NP_663567), xenopus (GENBANK Accession Nos. NP 001079061, NP 001079319 and NP_001121290), bovine (GENBANK Accession Nos. NP_001076084 and NP_001093776) and the diploblast Hydra (Guder, et al. (2006) *Development* 133(5):901-11; Augustin, et al. (2006) *Dev. Biol.* 296(1):62-7). Human Dkk-1 and Dkk-2 share 50% identity in their N-terminal domains and 70% identity in their C-terminal cysteine-rich domains. Moreover, it has been shown that the C-terminal domain of human dkk-1 and dkk-2, which contains the second cysteine-rich region, is sufficient for antagonism of Wnt activity in mammalian cells (Li, et al. (2002) *J. Biol. Chem.* 277, 5977-5981). Accordingly, while some embodiments embrace the expression of a full-length dkk protein, other embodiments embrace the expression of only a portion or fragment (i.e., less than full-length) of a dkk protein. In certain embodiments, said portion or fragment includes only one cysteine-rich domain of the dkk protein. In particular embodiments, said portion or fragment of dkk includes the carboxy-terminal cysteine-rich domain. By way of illustration, the C-terminal cysteine-rich domain of mouse Dkk2 is located between residues Met$^{172}$ and Ile$^{259}$ (Chen, et al. (2008) *J. Biol. Chem.* 283:23364-23370). In this respect, similar residues from other dkk proteins can be used. In particular embodiments, a fragment or portion of a dkk protein is intended to mean the 80 to 130 residue C-terminal amino acid residues of dkk, which include the C-terminal cysteine-rich domain.

In order to increase solubility of recombinant Dkk proteins in prokaryotic host cells, some embodiments feature fusion products containing the Dkk protein operably linked to a solubilization molecule. As used herein, the term operably linked is intended to mean that the Dkk protein sequence and solubilization molecule sequence are linked in such a manner that the Dkk protein and solubilization molecule are expressed as an in-frame fusion protein. Examples of solubilization molecules of use in the present invention include, but are not limited to, glutathione-S-transferase (GST), thioredoxin (Trx) and N utilization substance A (NusA). The amino acid sequences of these solubilizing molecules are known in the art and available from sources such as GENBANK. Desirably, the solubilization molecules are obtained from or suitable for expression in a bacterial cell. By way of illustration, suitable GST sequences are available under GENBANK Accession Nos. YP_002329946 (*E. coli*), EAP71894 (*Ralstonia solanacearum*), and NP_251511 (*Pseudomonas aeruginosa*) Examples of suitable thioredoxin sequences are available under GENBANK Accession Nos. NP_756559 (*E. coli*), AAG08625 (*P. aeruginosa*), AAA87315 (*Bacillus subtilis*), and CAJ96056 (*R. eutropha*). Exemplary NusA proteins sequences are available under GENBANK Accession Nos. AAG08131 (*P. aeruginosa*), AAP10737 (*B. cereus*), AAN82367 (*E. coli*) and CAQ35398 (*R. solanacearum*).

In addition to a solubilization molecule, some embodiments of this invention embrace the inclusion of one or more protein purification tags in the fusion protein of the invention. More specifically, to separate or isolate the dkk2 protein and/or solubilization molecule from other proteins or contaminates, it may be desirable to directly fuse a protein purification tag to the dkk2 protein and/or solubilization molecule. As illustrated herein, a Hexa-His tag was fused to the thioredoxin molecule, whereas an S-tag was fused to the C-terminal fragment of Dkk-2. It is contemplated that a tag can be directly fused to the protein to be purified, or be separated from said protein by a cleavage sequence and/or spacer, thereby allowing for removal of the tag from the protein of interest. It is contemplated that spacers can be employed to allow for efficient protease cleavage in cases where the cleavage site may be obstructed by neighboring sequences. Such spacers are known in the art and routinely used in protein fusions. Examples of cleavage sequences include, but are not limited to, thrombin cleavage sequences, enterokinase cleavage sequences, Cathepsin D cleavage sequences and the like. Other suitable cleavage sequences are known in the art and a comprehensive list of proteases and their cognate cleavage sequences is available from the MEROPS database (see Rawlings, et al. (2002) *Nucl. Acids Res.* 30:343-346). In particular embodiments, the fusion protein of the invention contains one or more thrombin cleavage sequences.

As disclosed herein, particular fusion proteins are contemplated for producing soluble, active dkk. Components of the fusion proteins include one or more of a solubilization molecule (S), a protein purification tag (T), a cleavage sequence (C), spacer (X), and dkk (D). Fusion proteins embraced by the present invention include those with the structures:

$(S)-(T_1)-(C_1)-(T_2)-(C_2)-(C_3)-(D)$;
$(S)-(T_1)-(C_1)-(T_2)-(C_2)-(D)$;
$(S)-(T)-(C_1)-(C_2)-(D)$;
$(S)-(C_1)-(T)-(C_2)-(X)-(D)$;
$(S)-(T_1)-(C_1)-(T_2)-(C_2)-(X)-(D)$;
$(S)-(C)-(X)-(D)$;
$(S)-(C)-(T)-(D)$; or
$(S)-(C)-(D)$

When more than one tag is employed, desirably the tags are different from one another; however, when more than one cleavage sequence is employed, said cleavage sequences may be the same or different. In accordance with the above-referenced fusion proteins, particular embodiments embrace thioredoxin as the solubilization molecule (S), Hexa-His tag or S-tag as the protein purification tag (T), thrombin cleavage sequence or enterokinase cleavage sequence as cleavage sequences (C), polyglycine as the spacer (X), and dkk-2 as dkk (D). In specific embodiments, the dkk-2 protein is human.

In particular embodiments, fusion to thioredoxin as a solubilization molecule may also confer other benefits when fusion proteins disclosed herein are expressed by a prokaryotic host cell that has disabled genes involved in the thiol-disulfide balance. Such strains typically are characterized by having a mutation in glutathione reductase (gor) and thioredoxin reductase (TrxB) genes, and in some cases further include a mutation in the lacY1 gene (i.e., designated "B" strains). Examples of such strains include, but are not limited to, ORIGAMI™, ORIGAMI™ B, ROSETTA-GAMI™ and ROSETTA-GAMI™ B. In normal strains, there is a high reducing potential in the cytoplasm and disulfide bonds are usually only formed in the periplasmic space. The presence of these two mutations, gor and TrxB alters this balance and these mutations have been shown to increase the efficiency of disulfide bond formation of recombinant proteins in the cytoplasm of *E. coli* (Aslund, et al. (1999) *inNovations* 10:11-12; Prinz, et al. (1997) *J. Biol. Chem.* 272:15661-15667). The presence of the Trx sequences as part of a fusion protein may provide further advantages in such strains since it may be able to catalyze disulfide bond formation in the cytoplasm (Stewart, et al. (1998) *EMBO J.* 17:5543-5550). Accordingly, particular embodiments embrace prokaryotic host cells having a mutation in one or both of its gor and TrxB genes. In other embodiments, the prokaryotic host cells further includes a mutation in the lacY1 gene.

As used herein, "prokaryote" and "prokaryotic cell" refer to cells which do not contain a nucleus and whose chromosomal material is thus not separated from the cytoplasm. Prokaryotes include, for example, bacteria. Prokaryotic host cells particularly embraced by the present invention include those amenable to genetic manipulation and growth in culture. Exemplary prokaryotes routinely used in recombinant protein expression include, but are not limited to, *E. coli*, *Bacillus licheniformis* (van Leen, et al. (1991) *Bio/Technology* 9:47-52), *Ralstonia eutropha* (Srinivasan, et al. (2002)

*Appl. Environ. Microbiol.* 68:5925-5932), *Methylobacterium extorquens* (Belanger, et al. (2004) *FEMS Microbiol. Lett.* 231(2):197-204), *Lactococcus lactis* (Oddone, et al. (2009) *Plasmid* 62(2):108-18) and *Pseudomonas* sp. (e.g., *P. aerugenosa, P. fluorescens* and *P. syringae*). Prokaryotic host cells can be obtained from commercial sources (e.g., Clontech, Invitrogen, Stratagene and the like) or repositories such as American Type Culture Collection (Manassas, Va.). In particular embodiments, the prokaryotic host cell is *E. coli*. The expression of recombinant proteins in *E. coli* is well-known in the art. Protocols for *E. coli*-based expression systems are found in U.S. Pat. Nos. 6,245,539, 5,606,031, 5,420,027, 5,151,511, and RE33,653, among others.

The prokaryotic host cells of the invention are recombinant in the sense that they have been genetically modified for the purposes of harboring and expressing nucleic acids encoding a dkk protein, or a portion thereof. Accordingly, the present invention also embraces an expression construct for expressing all or a portion of a dkk protein, or a fusion protein containing the same. For the purposes of the present invention, an expression construct is a nucleic acid molecule that contains all the appropriate regulatory sequences necessary for expression of a dkk protein or a fragment of a dkk protein, or a fusion protein containing the same, in a prokaryotic host cell. Such regulatory sequences include, for example, promoter and terminator sequences, which are recognized by the transcription machinery of a prokaryotic host cell. In some embodiments, the regulatory sequences provide for constitutive expression of a dkk protein, or portion thereof. In other embodiments, the regulatory sequences provide for inducible expression of a dkk protein, or portion thereof. Regulatory sequences for constitutive or inducible expression, e.g., by molecule such as IPTG, tetracycline, or heavy metals, are well-known in the art and typically present in conventional prokaryotic expression vectors available from commercial sources. By way of exemplification, the prokaryotic expression vector pET32a contains the necessary regulatory sequences for expression in a prokaryotic host cell.

Results presented herein demonstrate that the use of a combination of the above-reference molecules in a fusion protein allows for successful prokaryotic expression of a dkk protein that involves formation of five separate disulfide bonds to achieve the proper secondary structure. In this respect, an efficient method for producing soluble, active Dkk protein, or a fragment thereof, has now been developed. According to this method of the invention, a culture of prokaryotic host cells, which expresses all or a portion of a dkk protein encoded by an expression construct, are grown under suitable growth conditions; the prokaryotic host cells are isolated and lysed; the soluble portion of the prokaryotic cell lysate is isolated; and the dkk protein from the soluble portion is purified. Prokaryotic host cells harboring an expression construct encoding all or a portion of a dkk protein can be prepared using conventional methods. For example, expression constructs disclosed herein can be introduced into suitable prokaryotic host cells by conventional methods such as electroporation or calcium phosphate or calcium chloride co-precipitation. Suitable methods for transforming and selecting for recombinant host cells can be found in Sambrook, et al. (1989) *A Laboratory Manual*, or other laboratory manuals. Recombinant host cells can be cultured under conventional growth conditions, which can optionally include the addition of agents that induce protein expression from the expression construct. Such agents include IPTG, tetracycline and heavy metals. Once the recombinant host cells have been cultured for a time sufficient to express the dkk protein or portion thereof, the cells are isolated (e.g., by centrifugation or filtration) and lysed (e.g., by detergent or physical means) by detergent and/or physical means). The soluble portion of the lysate is then isolated (e.g., by centrifugation or filtration) and the dkk protein, or dkk protein fragment, is purified from said soluble portion. The dkk protein, or dkk protein fragment, can be purified by various means depending on the whether the dkk protein or dkk fragment is produced as a fusion protein with or without a tag. For example, when the dkk protein, or dkk protein fragment, is produced as a fusion protein with a tag, the tag can be used to purify the fusion protein from the contaminants present in the soluble portion of the cell lysate. According to particular embodiments, the tag is bound to a metal chelate column. In addition to, or as an alternative to the use of a tag, the dkk protein can be purified by high-pressure liquid chromatography (HPLC), e.g., as exemplified herein.

Figure 1B:
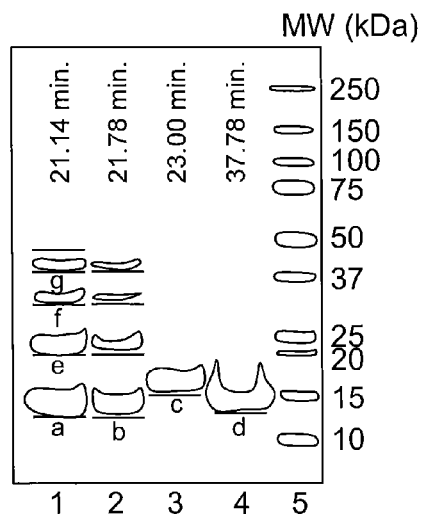
FIG. 1B is a SDS-PAGE gel showing elution fractions from HPLC purification. The elution time for each fraction is labeled in the corresponding lane. Protein bands in each fraction are indicated by dashed lines with letters below.
Figure 2:
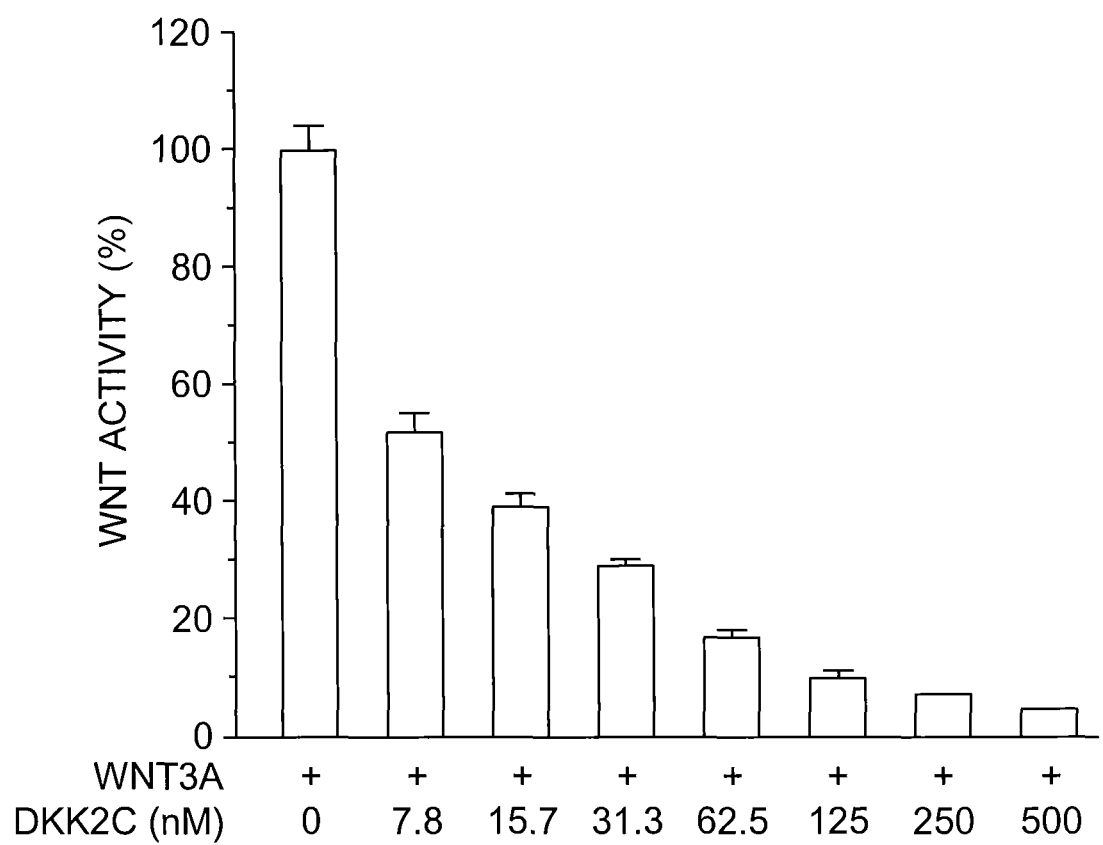
FIG. 2 shows a dose-response curve of wnt activity with recombinant Dkk2C. Cells transfected with a wnt-dependent reporter gene were exposed to various amounts of Dkk2C and evaluated in terms of the ability of the Dkk2C to inhibit wnt activity.

Examination of the soluble Dkk protein derived from host cell lysates exemplified herein showed that some recombinant dkk protein was produced that was incomplete in adopting the proper disulfide bonds. However, HPLC was able to completely separate the appropriately folded protein from inactive forms, resulting in a highly active, pure dkk protein. In contrast, 60% of the proteins found in conventional preparations of dkk protein were inactive, concatameric forms of dkk. Accordingly, the instant method is a significant improvement over the art in that it provides a protein preparation, the content of which is composed of greater than 90% natively folded, biologically active, recombinant dkk protein, as evidenced by a single band on SDS-PAGE (FIG. 1B) and the ability to inhibit Wnt activity (FIG. 2). Moreover, the instant method is an improvement over conventional methods in that additional solubilization steps are not required upon isolation of the recombinant dkk protein. Accordingly, in particular embodiments, the method of the present invention consists of the steps of a) growing a culture of prokaryotic host cells that express all or a portion of a dkk protein encoded by an expression construct;

b) isolating said prokaryotic host cells;

c) lysing said prokaryotic host cells;

d) isolating the soluble portion of said prokaryotic cell lysate; and e) purifying said dkk protein from said soluble portion.

In so far as the example provided herein demonstrates successful prokaryotic expression of an active soluble version of only one of the CRDs of Dkk, it is anticipated that the instant constructs and methods will also achieve prokaryotic expression of soluble forms of the intact dkk protein itself as well as other portions of dkk including the amino CRD. Expression constructs, fusion proteins, prokaryotic host cells and the method of this invention all find application in the production of soluble, active dkk protein, or portions thereof, for use in protein structure and function analysis and in drug screening assays or rational drug discovery of Wnt-targeted therapeutics. In this respect, de-regulation of Wnt signaling pathways has been implicated in many human diseases, ranging from cancers to skeletal disorders. As such, it is contemplated that mimics or analogs of Dkks could be used as inhibitors of Wnt signaling in cancer therapy. For example, expression of Dkk-3 was significantly down-regulated in primary non-small cell lung carcinomas, and expression of exogenous Dkk-3 gene in non-small cell lung carcinoma cells inhibited cell growth (Tsuji, et al. (2001) *Biochem. Biophys. Res. Commun.* 289:257-63). Likewise, expression of Dkk-3 and dominant-negative LRP5 mutant in Saos-2 cells significantly reduces invasion capacity and cell motility (Hoang et al. (2004) *Cancer Res.* 64:2734-2739). As such, structural analysis of recombinant Dkks will provide insight into features necessary for inhibiting Wnt signaling and in the design of therapeutics for the treatment of cancer.

The invention is described in greater detail by the following non-limiting examples.

EXAMPLE 1

Construction of Thioredoxin (Trx)-Dkk2C Expression Vector

The cDNA that encodes Dkk2C was subcloned into the pET32a vector (Novagen). The linearized pET32a vector contains NdeI and BamHI restriction sites, as well as a T7 promoter and the coding sequence for ampicillin resistance. The pET32a vector was fused with a sequence coding for the 109-amino acid thioredoxin (Trx) protein. In addition, a sequence coding for a $His_6$-tag peptide was added to the segment coding for the C-terminal end of thioredoxin protein followed by a thrombin cleavage sequence and a sequence coding for an S-tag peptide. The cDNA of Dkk2C was inserted into pET32a vector after the S-tag addition using the NdeI and BamHI sites. Another thrombin cleavage site was then added between the S-tag coding sequence and the Dkk2C sequence in order to allow a subsequent removal of the S-tag sequence from the Dkk2C segment by treatment with thrombin. The amino acid sequence of the resultant Trx-Dkk2C fusion protein is provided as SEQ ID NO:1, wherein the positions of the various elements of the fusion protein are listed in Table 1.

TABLE 1

| Functional Element | Amino Acid Residues in SEQ ID NO: 1 |
| --- | --- |
| Thioredoxin sequence | 1-109 |
| Hexa-His Tag sequence | 117-122 |
| First Thrombin cleavage sequence | 126-131 |
| S-Tag sequence | 134-148 |
| Enterokinase cleavage sequence | 154-158 |
| Second Thrombin cleavage sequence | 160-165 |
| Dkk2c coding sequence | 166-253 |

The Trx-Dkk2C fusion expression vector was transformed into E. con_ DH5a strains (Invitrogen) and the presence of the appropriate nucleotide sequence for the fusion gene was confirmed by sequence analysis.

EXAMPLE 2

Expression of Trx-Dkk2C Fusion in ORIGAMI™ B Strains

The Trx-Dkk2C fusion expression vector was subsequently transformed into an ORIGAMI™ B strain of E. coli (Invitrogen) for protein production. ORIGAMI™ B host strains carry are derived from a lacZY mutant of BL21, which additionally contains trxB/gor mutations. The genotype of ORIGAMI™ B cells is F⁻ ompT $hsdS_B(r_B^- m_B^-)$ gal dcm lacY1 ahpC gor522::Tn10 trxB ($Kan^R$, $Tet^R$). Cells were grown in Luria-Bertani media with shaking at 220 rpm at 37° C. Protein expression was induced by the addition of 0.2 mM isopropyl-1-thio-β-D-galactoside (IPTG) when cells were at about mid-log phase ($OD_{600\ nm}$ approximately 0.5) and the culture was shifted to 16° C. after IPTG addition and incubated for an additional 16 hours. SDS-PAGE (sodium dodecyl sulfate polyacrylamide gel electrophoresis) was used to verify protein expression: 1 ml aliquots of cell cultures were removed just before IPTG induction and at 16 hours post-induction. Cells were centrifuged at 3000 rpm for 2 minutes, and the isolated pellet was resuspended by adding 100 µl 1×SDS loading buffer (Invitrogen, Carlsbad, Calif.). Cell disruption and denaturation were allowed to proceed by heating at 100° C. for 5 minutes before the sample was loaded on to a 4-12% Tris-HCl gel (Invitrogen). All SDS-PAGE gels were visualized using COOMASSIE® blue staining. The results of this analysis indicated that, after induction with IPTG, there was extensive synthesis of a 27.8 kDa band corresponding to the predicted size of the Trx-Dkk2C fusion protein.

The bulk of the cells induced for 16 hours was harvested by centrifugation at 5000×g for 20 minutes at 4° C. Cell pellets were resuspended by addition of lysis buffer (25 mM Bis-Tris, pH 6.8, 500 mM NaCl, 5 mM $MgCl_2$, and 2% Glycerol) complemented with a tablet of protease inhibitor cocktail (Roche Diagnostics, Germany). The suspensions were kept on ice to facilitate cell lysis. To complete lysis, cells were subjected to high pressure using a Microfluidizer Processor (Model M110L) (Microfluidics, Newton, Mass.). The insoluble fraction of the cell lysates was removed from the soluble fraction through centrifugation at 13,000 rpm for 20 minutes at 4° C.

EXAMPLE 3

His-Tag Purification of Trx-Dkk2C

Either of the His-Tag or the S-tag affinity peptides could be used for an initial purification of the fusion protein. By way of illustration, the His-Tag was used with Immobilized Metal Affinity Chromatography (IMAC). Purification was carried out by incubating the cell lysates of Example 2 with Ni-NTA charged resin (Invitrogen, Carlsbad, Calif.) and gentle agitation for 5 hours at 4° C., thereby allowing the $His_6$-region of the Trx-Dkk2C protein to bind to the Ni-NTA. After this incubation step, the Trx-Dkk2C fusion-charged beads were transferred into a column and washed with elution buffer (25 mM Bis-Tris, pH 6.8, 500 mM NaCl, 5 mM $MgCl_2$, and 2% Glycerol) containing gradually increasing concentration of imidazole. Elution fractions were collected and characterized by SDS-PAGE. Although there was elution of a variety of proteins with the low imidazole washes (20 and 50 mM), the majority of the Trx-Dkk2C fusion protein was eluted from the column only after elution buffer containing 200 mM imidazole was applied, with even more material eluting with the first 500 mM imidazole wash. After further elution with 500 mM imidazole very little material was eluted.

EXAMPLE 4

Removal of Artificial Elements From Dkk Sequences

After IMAC purification, the target protein Dkk2C was cleaved from the Trx-Dkk2C fusion by removing the thioredoxin-tag, $His_6$-tag and S-tag regions with thrombin. Pooled fractions of Trx-Dkk2C fusion from Example 3 were incubated with thrombin from human plasma (Calbiochem, EMD Chemicals Inc., Darmstadt, Germany) (250 µg/L of original culture) with gentle agitation at room temperature. At intervals, the extent of digestion was determined by SDS-PAGE. After digestion was complete, benzamidine-agarose (Invitrogen, Carlsbad, Calif.) was added to the cleavage reaction to bind thrombin and terminate digestion. Subsequently, the benzamidine-agarose was pelleted by centrifugation at low speed (~100×g) to remove the cleavage products.

As listed in Table 1, there are two thrombin cleavage sites in the Trx-Dkk2C fusion protein, one located just before the S-tag sequence and one immediately after the S-tag. In principle, both of these cleavage sites should be cleaved upon completion of the digestion by thrombin. Based on the SDS-PAGE analysis of the thrombin digestion products, the first cleavage site located between the $His_6$-tag and the S-tag segments was completely cleaved 2 days after thrombin addition, as noted by the complete disappearance of the 27.8 kDa band (intact Trx-Histag-Stag-Dkk2c). However, the S-tag portion could not be removed from all of the Dkk2C fusion proteins completely, as evidenced by the continued presence of a 13.9 kDa band after 49 hours of thrombin addition. Even after incubation was continued for several days, a 13.9 kDa band persiste, suggesting that the second cleavage site, which is located after S-tag, is not as accessible thereby decreasing "complete" digestion. It is contemplated that the inaccessibility of this site is due to its close proximity to the tightly folded Dkk2C which may shield the cleavage site to some extent.

EXAMPLE 5

HPLC Purification of DKK

The products of the thrombin cleavage reaction in Example 4 were dialyzed against 5% acetic acid, and subsequently purified by HPLC (High Pressure Liquid Chromatography) with a ZORBAX300SB-C18 column (Agilent). Elution of Dkk2c from the column was by a gradient concentration of acetonitrile, which is plotted as a function of time in FIG. 1A. A profile of the HPLC elution is also shown in FIG. 1A and the fractions at elution times of 21.14, 21.78, 23.00 and 37.78 minutes were analyzed by SDS-PAGE (FIG. 1B).

The molecular weight of Dkk2C was predicted to be approximately 10.2 kDa. The bands closest to this weight (bands a-d, FIG. 1B) were characterized by electrospray ionization mass spectroscopy (ESIMS). Results of this protein identification method demonstrated that the a-c bands (FIG. 1B) in the 21.14-, 21.78- and 23.00-minute fractions, respectively, were Dkk2C protein, while band d in the 37.78-minute fraction was thioredoxin protein. Notably, in the 21.14- and 21.78-minute fractions, there were other bands, labeled as bands e-g (FIG. 1B). The corresponding molecular weight of these bands was ~20, 30 and 40 kDa, respectively. Protein identification characterized these bands as Dkk2C proteins, suggesting that the bands e, f and g were respectively dimeric, trimeric and tetrameric forms of Dkk2C. These oligomeric forms made up a minor portion of the Dkk when compared to the total monomeric forms in lanes 1, 2 and 3, whereas in the product made from resolubilized inclusion bodies, concatameric forms made up 60% of the protein (Gregory, et al. (2003) supra). The presence of these bands in the SDS-gel indicates that there was some degree of cross-linking between the recombinant molecules, though not nearly as extensive as observed using conventional methods.

EXAMPLE 6

NMR Analysis of the Final Product

The protein folding status of Dkk2C was further characterized by 1D $^1H$ NMR spectroscopy and 2D $^1H$-$^1H$ NOESY. Each of the HPLC fractions at 21.14, 21.78 and 23.00 minutes was pooled individually, concentrated and then characterized by NMR spectroscopy. The peaks in 1D $^1H$ spectrum and 2D $^1$-$^1H$ NOESY of the fraction at 23.00 minute spread in an abroad range, whereas other fractions displayed a crowded spectrum, suggesting that only the fraction at 23.00 minutes, which contained a single band on SDS-PAGE, was folded. In addition, the Dkk2C fraction at 23.00 minutes efficiently inhibited canonical Wnt signaling. Taken together, the results of NMR studies and biological activity indicate that the Dkk2C fraction at 23.00 minutes was natively folded recombinant protein, which is useful in structural studies of the Dkk2C protein.

NMR spectroscopy and gene reporter assay demonstrated that Dkk2C fraction at 23.00 minutes was folded and also efficiently inhibited canonical Wnt signaling activity, while other factions were unfolded. On SDS-PAGE, the folded Dkk2C faction contained a single band at approximately 15 kDa (band c in FIG. 1B), which was higher than those of unfolded fractions (bands a and b in FIG. 1B) and higher than the theoretical molecular weight calculated from the amino acid sequence of Dkk2C (10.2 kDa). The higher position of Dkk2C on SDS-PAGE was likely due to the network of disulfide bridges that keeps Dkk2C folded or at least partially folded even under the denaturing conditions of SDS-PAGE. This is supported by the observation that when the Dkk2C protein was heated at 100° C. for a long period of time prior to being loaded on the gel, a band at the same position as the unfolded fractions (bands a and b) was observed. Moreover, the longer Dkk2C was heated, the more intense this lower band became.

EXAMPLE 7

Effects of Dkk2C on Wnt Activity

NIH 3T3 cells were seeded in 24-well plates at $4 \times 10^5$ cells/well and transfected with a LEF-1 luciferase reporter plasmid, an EGFP expression plasmid and a lacZ plasmid (total of 0.5 μg DNA/well) by using LIPOFECTAMINE Plus (Invitrogen) under conditions described by the manufacturer. Twenty-four hours later, cells were treated for 6 hours with Wnt3a-conditioned medium (50 ng/ml) and various amounts of the Dkk2C protein were added (see FIG. 2). As a control, cells were also treated with Wnt3a-conditioned medium alone. At the end of the 6-hour treatment, the cells were lysed and luciferase activity in the lysate from each well was determined by luminescence and normalized against the fluorescence intensity of the green fluorescent protein (EGFP). The activity from control cells treated with Wnt3a only was taken as 100%. Two experiments were conducted individually and the average values were taken as the results. The results of this experiment are shown in FIG. 2, where a dose-response curve showed high levels of inhibition of wnt activity by the bacterially-derived, soluble, recombinant Dkk2C.

What is claimed is:

1. A method for producing soluble, active Dickkopf (Dkk) protein, or a portion thereof, comprising
   a) growing a culture of prokaryotic host cells that express all or a portion of a Dkk protein as a fusion protein encoded by an expression construct, wherein said fusion protein comprises all or a portion of a Dkk protein fused to a solubilization molecule;
   b) isolating said prokaryotic host cells;
   c) lysing said prokaryotic host cells;
   d) isolating the soluble portion of said prokaryotic cell lysate; and
   e) purifying said fusion protein from said soluble portion thereby producing soluble, active Dkk protein, or a portion thereof.

2. The method of claim 1, wherein step (a) includes adding isopropyl-1-thio-β-D-galactoside to the culture of prokaryotic host cells.

3. The method of claim 1, wherein the fusion protein further comprises a protein purification tag.

4. The method of claim 3, wherein the fusion protein further comprises one or more cleavage sequences located between the protein purification tag or solubilization molecule and the Dkk protein.

5. The method of claim 1, wherein the expression construct comprises a portion of the Dkk coding sequence and said portion comprises only one cysteine-rich domain.

6. The method of claim 5, wherein said cysteine-rich domain is a carboxy-terminal cysteine-rich domain.

7. The method of claim 1, wherein said expression construct is derived from a prokaryotic expression vector.

8. The method of claim 7, wherein said prokaryotic expression vector is pET32a.

9. The method of claim 1, wherein said Dkk protein is selected from the group consisting of Dkk-1, Dkk-2, Dkk-3 and Dkk-4.

10. The method of claim 9, wherein said Dkk protein is Dkk-2.

11. The method of claim 1, wherein said prokaryotic host cells have a mutation in a trxB gene, a gor gene or both said trxB gene and said gor gene.

12. The method of claim 11, wherein said prokaryotic host cells further have a mutation in a lacy1* gene.

13. The method of claim 1, wherein the isolation step (d) is carried out by centrifugation.

14. The method of claim 1, wherein said purification step (e) comprises the use of a metal chelate column.

15. The method of claim 1, wherein said purification step (e) comprises an HPLC step.

16. An expression construct comprising nucleic acids encoding all or a portion of Dickkopf (Dkk)-2 as a fusion protein, wherein said fusion protein comprises all or a portion of a Dkk protein fused to a solubilization molecule.

17. The expression construct of claim 16, further comprising nucleic acids encoding a protein purification tag.

18. The expression construct of claim 16, wherein said Dkk-2 protein is soluble when expressed in a prokaryotic host cell.

19. A prokaryotic host cell comprising an expression construct encoding a portion of a Dkk protein fused to a solubilization molecule, wherein said portion comprises only one cysteine-rich domain of the Dkk protein.

20. The prokaryotic host cell of claim 19, wherein the Dkk protein is the Dkk-2 protein.

21. The prokaryotic host cell of claim 19, wherein said cysteine-rich domain is the C-terminal cysteine-rich domain of the Dkk protein.

22. The prokaryotic host cell of claim 19, wherein the Dkk protein is soluble when expressed in the prokaryotic host cell.

23. A prokaryotic host cell comprising an expression construct encoding all or a portion of Dkk-2 protein fused to a solubilization molecule.

24. The prokaryotic host cell of claim 23, wherein said prokaryotic host cell has a mutation in a trxB gene, a gor gene or both said trxB gene and said gor gene.

* * * * *

SEQUENCE LISTING

```
<160> NUMBER OF SEQ ID NOS: 1

<210> SEQ ID NO 1
<211> LENGTH: 253
<212> TYPE: PRT
<213> ORGANISM: Artificial sequence
<220> FEATURE:
<223> OTHER INFORMATION: Synthetic polypeptide

<400> SEQUENCE: 1

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Asp Lys Ala Leu
145                 150                 155                 160

Val Pro Arg Gly Ser Met Pro His Ile Lys Gly His Glu Gly Asp Pro
                165                 170                 175

Cys Leu Arg Ser Ser Asp Cys Ile Asp Gly Phe Cys Cys Ala Arg His
                180                 185                 190

Phe Trp Thr Lys Ile Cys Lys Pro Val Leu His Gln Gly Glu Val Cys
            195                 200                 205

Thr Lys Gln Arg Lys Lys Gly Ser His Gly Leu Glu Ile Phe Gln Arg
        210                 215                 220

Cys Asp Cys Ala Lys Gly Leu Ser Cys Lys Val Trp Lys Asp Ala Thr
225                 230                 235                 240

Tyr Ser Ser Lys Ala Arg Leu His Val Cys Gln Lys Ile
                245                 250
```